United States Patent
Shinoda

(10) Patent No.: US 10,027,854 B2
(45) Date of Patent: Jul. 17, 2018

(54) IMAGE PROCESSING APPARATUS AND METHOD TO GENERATE IMAGE DATA FOR PRINTING ON SKIN ATTACHABLE SHEET BASED ON DISCOLORED SKIN REGION AND COLOR OF SURROUNDING SKIN

(71) Applicant: Panasonic Intellectual Property Management Co., Ltd., Osaka (JP)

(72) Inventor: Masayo Shinoda, Tokyo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 15/430,406

(22) Filed: Feb. 10, 2017

(65) Prior Publication Data
US 2017/0251130 A1    Aug. 31, 2017

(30) Foreign Application Priority Data
Feb. 29, 2016  (JP) .................................. 2016-037336

(51) Int. Cl.
*H04N 1/62* (2006.01)
*H04N 1/60* (2006.01)
(Continued)

(52) U.S. Cl.
CPC .......... *H04N 1/628* (2013.01); *A45D 44/002* (2013.01); *A61K 8/0204* (2013.01); *A61Q 1/02* (2013.01);
(Continued)

(58) Field of Classification Search
None
See application file for complete search history.

(56) References Cited

U.S. PATENT DOCUMENTS 8,437,540 B2 *  5/2013  Stephan ................ G06T 7/0012
                                                     382/162
9,384,543 B2 *  7/2016  Stephan ................ A61B 5/0077
(Continued)

FOREIGN PATENT DOCUMENTS

JP       3-157313       7/1991
JP       9-302294      11/1997
(Continued)

OTHER PUBLICATIONS

The Extended European Search Report dated Jun. 30, 2017 for the related European Patent Application No. 17155937.0.

*Primary Examiner* — Scott A Rogers
(74) *Attorney, Agent, or Firm* — Greenblum & Bernstein, P.L.C.

(57) ABSTRACT

An image processing apparatus generates image data used in printing an image on a sheet being attachable to skin. The image processing apparatus includes: an image acquirer that acquires a skin image picked up from the skin; an image analyzer that extracts, from the skin image, a discolored region differing in color from surrounding skin by at least a predetermined level, and surrounding color being color of the skin surrounding the discolored region; a grouping processor that groups a plurality of the discolored regions, and determines an inclusive region for each region group which is a cluster of the grouped plurality of discolored regions or one discolored region not having been grouped, to include the one or a plurality of the region groups; and a printing controller that generates image data having a content of printing a pigment material that causes color of the inclusive region to approximate the surrounding color, on a region corresponding to the inclusive region in the sheet.

10 Claims, 13 Drawing Sheets

(51) Int. Cl.

| | |
|---|---|
| *H04N 1/00* | (2006.01) |
| *G06K 15/02* | (2006.01) |
| *G06K 9/46* | (2006.01) |
| *G06K 9/34* | (2006.01) |
| *G06K 9/00* | (2006.01) |
| *G06T 7/90* | (2017.01) |
| *A61K 8/02* | (2006.01) |
| *A61Q 1/02* | (2006.01) |
| *A61F 13/00* | (2006.01) |
| *A45D 44/00* | (2006.01) |

(52) U.S. Cl.
CPC ......... *G06K 9/00281* (2013.01); *G06K 9/342* (2013.01); *G06K 9/4652* (2013.01); *G06K 15/021* (2013.01); *G06K 15/188* (2013.01); *G06T 7/90* (2017.01); *H04N 1/00005* (2013.01); *H04N 1/00023* (2013.01); *H04N 1/00034* (2013.01); *H04N 1/00039* (2013.01); *H04N 1/00092* (2013.01); *H04N 1/60* (2013.01); *A45D 2044/007* (2013.01); *A61F 2013/00153* (2013.01); *A61F 2013/00378* (2013.01); *A61K 2800/10* (2013.01); *A61K 2800/805* (2013.01); *A61K 2800/87* (2013.01); *G06K 2215/0094* (2013.01); *G06K 2215/0097* (2013.01)

(56) References Cited

U.S. PATENT DOCUMENTS

| | | | |
|---|---|---|---|
| 9,526,315 B2 * | 12/2016 | Shinoda | A45D 40/261 |
| 2007/0003604 A1 | 1/2007 | Jones | |
| 2015/0059968 A1 * | 3/2015 | Shinoda | A61Q 1/02 |
| | | | 156/240 |
| 2017/0259599 A1 * | 9/2017 | Shinoda | G06T 7/90 |
| 2017/0311871 A1 * | 11/2017 | Kikuchi | A61B 5/444 |

FOREIGN PATENT DOCUMENTS

| | | |
|---|---|---|
| JP | 2003-044837 | 2/2003 |
| JP | 2012-203425 | 10/2012 |
| JP | 2014-140978 | 8/2014 |
| JP | 2015-043836 | 3/2015 |

* cited by examiner

FIG. 8  610

| FIRST GROUPING RULE | GROUP A PLURALITY OF DISCOLORED REGIONS BEING SPACED APART FROM EACH OTHER BY INTERVAL BEING EQUAL TO OR SMALLER THAN PREDETERMINED THRESHOLD VALUE |
|---|---|
| SECOND GROUPING RULE | GROUP A PLURALITY OF DISCOLORED REGIONS DIFFERING IN COLOR FROM EACH OTHER WITHIN PREDETERMINED RANGE |

FIG. 9  620

| FIRST GROUP SEPARATING RULE | SEPARATE REGION GROUP BASED ON COLOR SIMILARITY WHEN DIFFERENCE IN COLOR EXCEEDS PREDETERMINED RANGE |
|---|---|
| SECOND GROUP SEPARATING RULE | SEPARATE REGION GROUP BASED ON FACTOR TYPE WHEN A PLURALITY OF DISCOLORED REGIONS DIFFERING FROM EACH OTHER IN FACTOR TYPE ARE INCLUDED |
| THIRD GROUP SEPARATING RULE | SEPARATE REGION GROUP BASED ON POSITION, COLOR, OR FACTOR TYPE WHEN THE NUMBER OF DISCOLORED REGIONS IN REGION GROUP IS EQUAL TO OR GREATER THAN PREDETERMINED THRESHOLD VALUE |

FIG. 10  630

| FIRST INCLUSIVE REGION SETTING RULE | SET CIRCULAR REGION (ELLIPTICAL REGION) THAT CIRCUMSCRIBES REGION GREATER THAN THE WHOLE DISCOLORED REGIONS AS INCLUSIVE REGION |
|---|---|
| SECOND INCLUSIVE REGION SETTING RULE | SET ELLIPTICAL REGION THAT INCLUDES THE WHOLE DISCOLORED REGIONS BY MINIMUM AREA AS INCLUSIVE REGION |
| THIRD INCLUSIVE REGION SETTING RULE | SET ELLIPTICAL REGION THAT INCLUDES DISCOLORED REGIONS BY PREDETERMINED AREA RATIO AS INCLUSIVE REGION |

IMAGE PROCESSING APPARATUS AND METHOD TO GENERATE IMAGE DATA FOR PRINTING ON SKIN ATTACHABLE SHEET BASED ON DISCOLORED SKIN REGION AND COLOR OF SURROUNDING SKIN

BACKGROUND

1. Technical Field

The present disclosure relates to an image processing apparatus and an image processing method for generating image data for printing an image on a sheet attachable to skin.

2. Description of the Related Art

Conventionally, there exist techniques for making a discolored region of the skin, such as a spot on the cheeks, less noticeable (for example, see PTL 1). According to the technique described in PTL 1 (hereinafter referred to as "the conventional technique"), a discolored region of the skin is identified from a picked-up image of the skin, and a sheet attachable to the skin and on which the color of a non-discolored region is printed is generated in size equal to or greater than that of the discolored region. Such a conventional technique can make the discolored region of the skin less noticeable by a simple work of attaching the sheet to the skin.

CITATION LIST

Patent Literature

PTL 1: Unexamined Japanese Patent Publication No. 2015-43836
PTL 2: Unexamined Japanese Patent Publication No. 2014-140978
PTL 3: Unexamined Japanese Patent Publication No. H03-157313
PTL 4: Unexamined Japanese Patent Publication No. H09-302294
PTL 5: Unexamined Japanese Patent Publication No. 2012-203425
PTL 6: Unexamined Japanese Patent Publication No. 2003-44837

However, according to the conventional technique, generating and attaching the sheet take time and are troublesome, when a multitude of discolored regions exist on the skin. On the other hand, particularly on the cheeks of the face, often a multitude of small discolored regions such as spots and freckles are distributed. Accordingly, there exists demand for a technique according to which a plurality of discolored regions on the skin are made less noticeable with ease.

SUMMARY

One non-limiting and exemplary embodiment provides an image processing apparatus and an image processing method capable of easily making a plurality of discolored regions of the skin less noticeable.

In one general aspect, the techniques disclosed here feature an image processing apparatus that generates an image data used in printing an image on a sheet being attachable to skin. The image processing apparatus includes: an image acquirer that acquires a skin image picked up from the skin; an image analyzer that extracts, from the skin image, a discolored region differing in color from surrounding skin by at least a predetermined level, and surrounding color being color of the skin surrounding the discolored region; a grouping processor that groups a plurality of the discolored regions, and determines an inclusive region for each region group which is a cluster of the grouped plurality of discolored regions or one discolored region not having been grouped, to include the one or a plurality of the region groups; and a printing controller that generates the image data having a content of printing a pigment material that causes color of the inclusive region to approximate the surrounding color, on a region corresponding to the inclusive region in the sheet.

The present disclosure is capable of easily making a plurality of discolored regions of the skin less noticeable.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

It should be noted that, general or specific embodiments may be implemented as a system, a method, an integrated circuit, a computer program, or a recording medium, or any combination of a system, an apparatus, a method, an integrated circuit, a computer program, and a recording medium.

BRIEF DESCRIPTION OF THE DRAWINGS

FIG. 8 shows exemplary grouping rule information according to the present disclosure;

FIG. 9 shows exemplary group separating rule information according to the present disclosure;

FIG. 10 shows exemplary inclusive region setting rule information according to the present disclosure;

DETAILED DESCRIPTION

In the following, a detailed description will be given of one exemplary embodiment of the present disclosure with reference to the drawings.

System Structure

Firstly, a description will be given of the overview of a makeup supporting system that includes an image processing apparatus according to the present exemplary embodiment.

Figure 1:
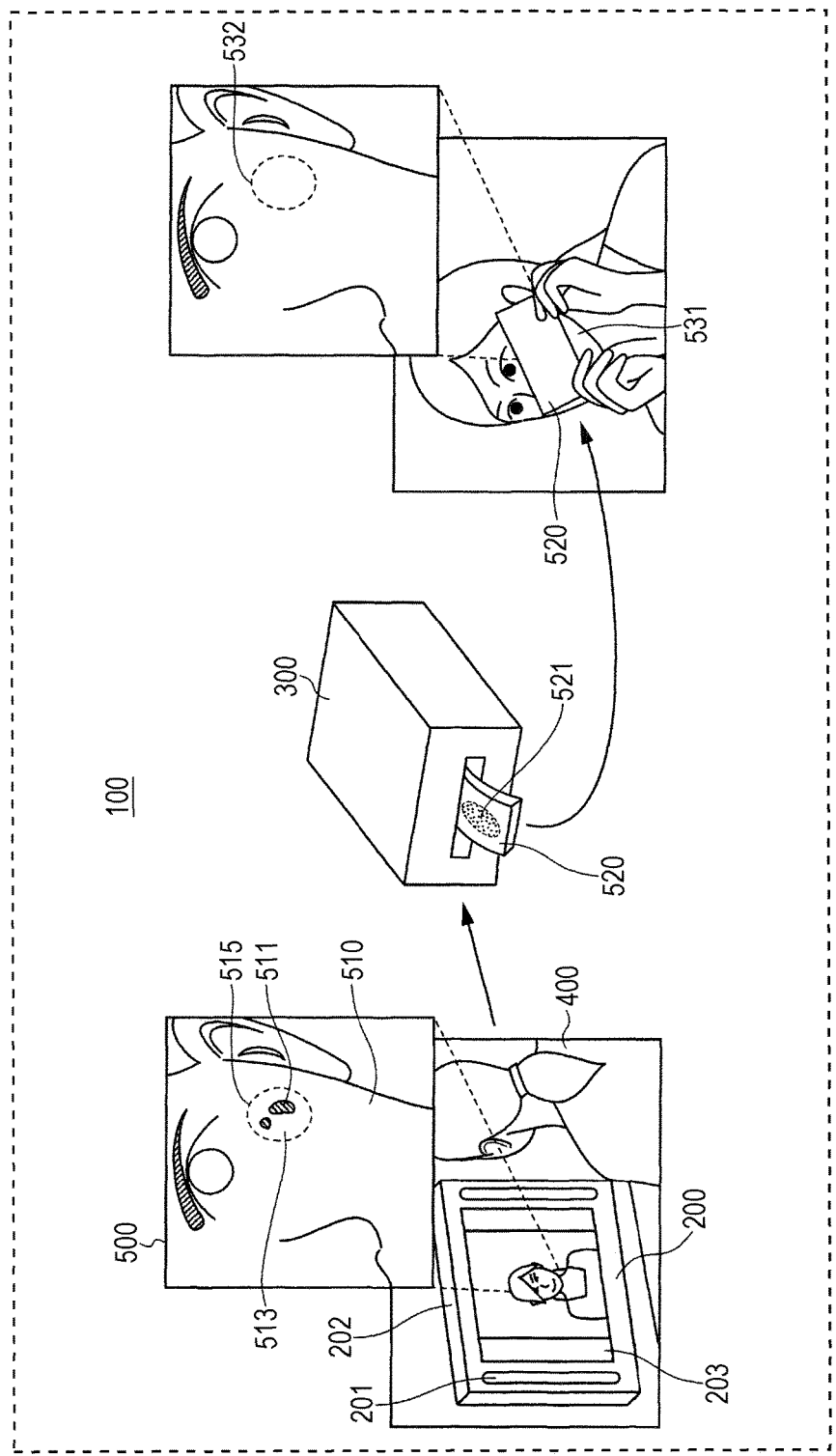
FIG. 1 is a schematic diagram showing the overview of an exemplary makeup supporting system according to the present disclosure.

FIG. 1 is a schematic diagram showing the overview of an exemplary makeup supporting system.

In FIG. 1, makeup supporting system 100 includes: image processing apparatus 200 that includes lighting 201, camera 202, and display 203 such as a liquid crystal display equipped with a touch panel; and printer apparatus 300 communicatively connected with image processing apparatus 200. Image processing apparatus 200 and printer apparatus 300 are disposed at, for example, a factory, a cosmetic shop, a beauty salon, a medical facility, a makeup room for grooming, an event site, or a home. Note that, image processing apparatus 200 may be a portable apparatus that can be carried with ease.

Image processing apparatus 200 picks up, with camera 202 disposed near display 203, an image of the face of user 400 positioned in front of display 203, with lighting 201 illuminated. Then, image processing apparatus 200 displays, on display 203, picked-up image 500 which is horizontally inverted (hereinafter referred to as "facial image 500"). That is, image processing apparatus 200 makes user 400 feel like looking in a mirror.

Further, image processing apparatus 200 extracts discolored regions 511 in skin image 510 from the obtained facial image 500 (or from the image before inversion), and determines inclusive region 515 that includes one or a plurality of discolored regions 511. Then, image processing apparatus 200 generates image data of an image that forms a region in the color of surrounding 513 of discolored regions 511 (hereinafter referred to as "the surrounding color") in the shape and size of inclusive region 515, and outputs the generated image data to printer apparatus 300.

Printer apparatus 300 prints an image on makeup sheet 520, which is attachable to skin 531, based on the image data output from image processing apparatus 200. For example, printer apparatus 300 prints an image on makeup sheet 520 being attached to a supporter (a mat) which can be peeled off.

More specifically, printer apparatus 300 applies a pigment material (a cosmetic material or the like) similar in color to the surrounding color to a region corresponding to inclusive region 515, to generate makeup sheet 520 on which covering region (a shielding layer, a skin color correcting color layer) 521 is formed. Printer apparatus 300 can print an image on a region at the skin-side surface of makeup sheet 520 corresponding to inclusive region 515 not only a pigment material but also, for example, a medication that promotes restoration of discolored regions 511.

Makeup sheet 520 has a surface that is tightly attached to skin 531 (hereinafter referred to as "the skin-side surface"), and the opposite surface (hereinafter referred to as "the external surface"). Printer apparatus 300 prints covering region 521 on predetermined one of the skin-side surface and the external surface. For example, by being tightly attached to skin 531, makeup sheet 520 allows covering region 521 printed on the skin-side surface to be transferred to skin 531. Alternatively, by being maintained to be attached to skin 531, makeup sheet 520 allows covering region 521 printed on the skin-side surface or the external surface to be borne on skin 531.

As described above, covering region 521 is formed in the color of the skin surrounding discolored regions 511. Accordingly, by being covered with covering region 521, in region 532 of the skin corresponding to inclusive region 515, discolored regions 511 become less noticeable.

That is, makeup supporting system 100 realizes makeup of solving unevenness in color of skin 531 with a simple and quick operation of attaching makeup sheet 520 to skin 531.

Note that, makeup sheet 520 does not make the user feel uncomfortable when attached to the user's skin, and is biocompatible. Specifically, makeup sheet 520 is a thin film having a layer of biocompatible polymer of, for example, polylactic acid, polyglycolic acid, polycaprolactone, copolymer of the foregoing, hyaluronic acid, chitosan and the like, and having a thickness of 10 nm to 500 nm inclusive. A thin film that can be used as makeup sheet 520 is described in, for example, PTL 2, and therefore a detailed description thereof is not given herein.

Further, the material (ink) used in printing by printer apparatus 300 and the specific structure of the members of printer apparatus 300 are described in, for example, PTL 3 to PTL 5, and therefore a detailed description thereof is not given herein.

Image processing apparatus 200 further determines inclusive region 515 as the base of covering region 521, in consideration of existence of a multitude of discolored regions 511 on skin 531.

Figure 2:
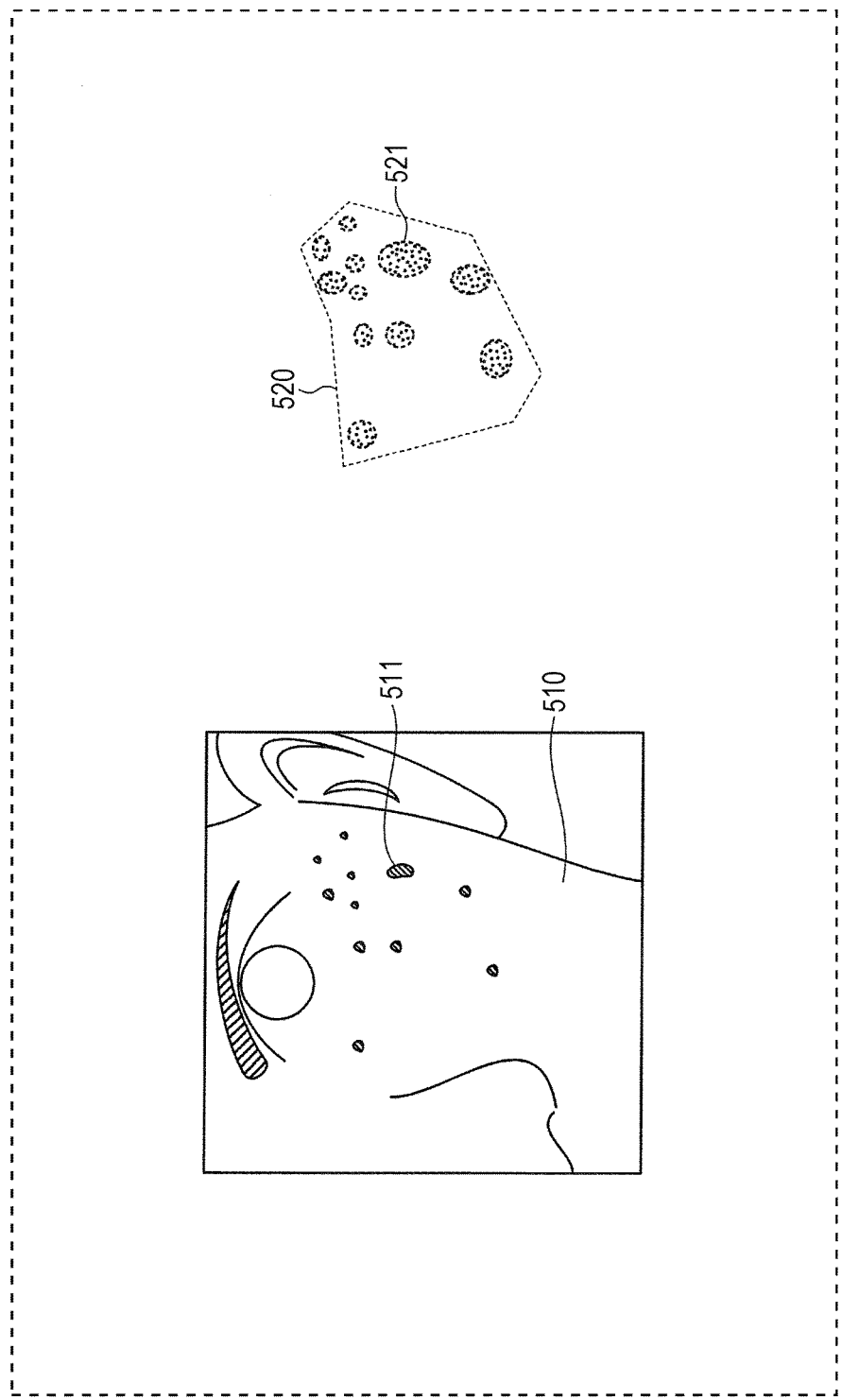
FIG. 2 illustrates exemplary appearance of the skin and an exemplary makeup sheet according to the present disclosure.

FIG. 2 illustrates the appearance of the skin on which a multitude of discolored regions 511 exist, and exemplary makeup sheet 520 in the case where inclusive region 515 is simply determined for each discolored region 511 of the skin. Note that, such an exemplary makeup sheet 520 is an exemplary makeup sheet that is generated from image data which is different from image data generated by image processing apparatus 200.

As shown in FIG. 2, in the case where inclusive region 515 is determined for each discolored region 511 for skin image 510 containing a multitude of discolored regions 511, a multitude of covering regions 521 corresponding to a multitude of inclusive regions 515 are disposed at makeup sheet 520.

However, as the number of covering regions 521 is greater, it becomes more difficult to correctly attach makeup sheet 520 to the skin.

Figure 3:
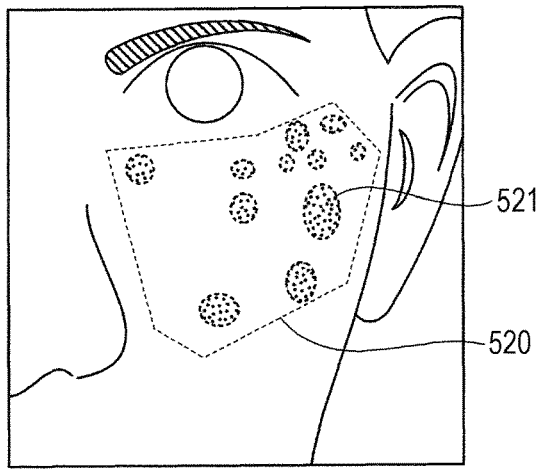
FIG. 3 illustrates a first exemplary state where the makeup sheet according to the present disclosure is attached.
Figure 4:
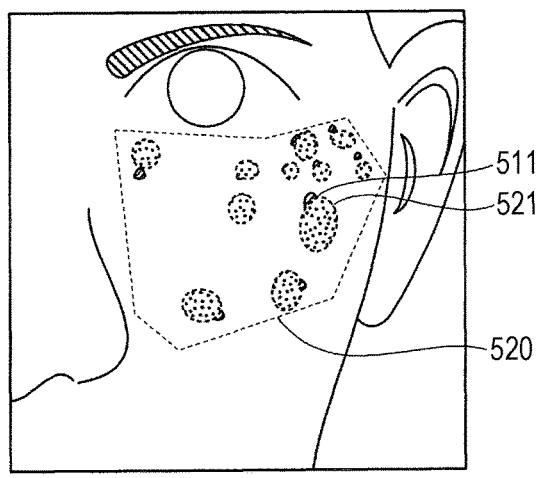
FIG. 4 illustrates a second exemplary state where the makeup sheet according to the present disclosure is attached.
Figure 5:
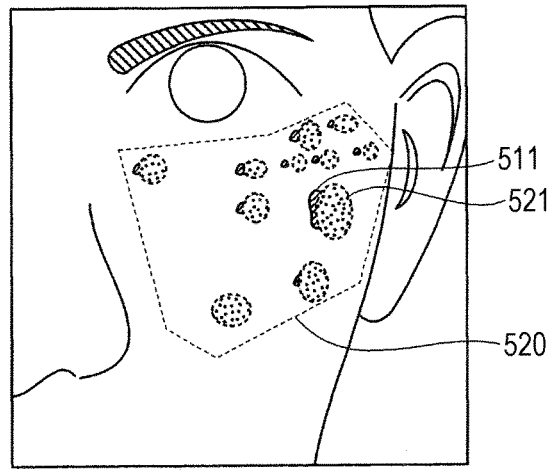
FIG. 5 illustrates a third exemplary state where the makeup sheet according to the present disclosure is attached.

FIG. 3 illustrates an exemplary state where makeup sheet 520 shown in FIG. 2 is attached correctly. FIG. 4 illustrates an exemplary state where makeup sheet 520 shown in FIG. 2 is attached at a wrong angle. FIG. 5 illustrates an exemplary state where makeup sheet 520 shown in FIG. 2 is attached at a wrong position.

As shown in FIG. 3, in the case where makeup sheet 520 is attached at the correct angle and position, discolored regions 511 are all covered with covering regions 521 and become less noticeable. On the other hand, as shown in FIGS. 4 and 5, when makeup sheet 520 is attached at a wrong angle or position, discolored regions 511 are not completely covered with covering regions 521 and instead exposed, becoming noticeable.

Accordingly, image processing apparatus 200 groups a plurality of discolored regions 511, and determines inclusive region 515 that includes a cluster of the grouped plurality of discolored regions 511 or one discolored region 511 not having been grouped (hereinafter referred to as "the region group").

Figure 6:
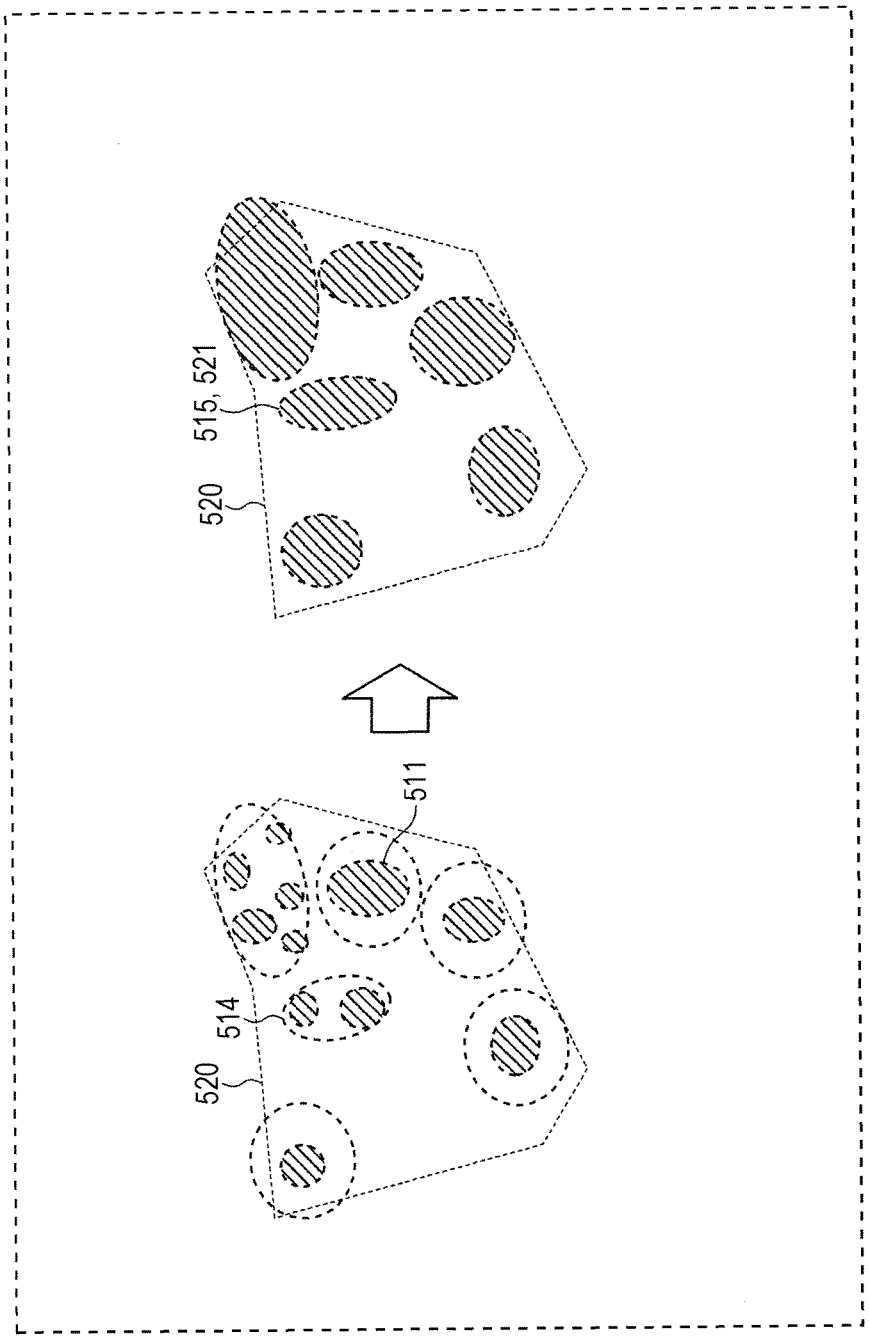
FIG. 6 illustrates an exemplary manner of grouping discolored regions and an exemplary makeup sheet according to the present disclosure.

FIG. 6 illustrates an exemplary manner of grouping discolored regions 511 and exemplary makeup sheet 520 generated by the grouping.

As shown in FIG. 6, image processing apparatus 200 groups, for example, discolored regions 511 being closer to each other, to set region group 514. Then, image processing apparatus 200 determines, for each region group 514, inclusive region 515 that includes discolored regions 511 belonging to that region group 514. Then, image processing apparatus 200 generates image data describing that such inclusive region 515 is covering region 521, and outputs the generated image data to printer apparatus 300.

Makeup sheet 520 generated in this manner can more surely cover a plurality of discolored regions 511, coping with deviation in attaching angle or position of a certain degree.

Note that, in the present exemplary embodiment, discolored regions 511 being the target of extraction may differ from each other in the factor of discoloring. That is, discolored regions 511 are categorized, by the type of discoloring factor (hereinafter referred to as "the factor type"), into pigmented spots, chloasma, nevus spilus, melanocytic nevus, Nevus of Ota, acquired dermal melanocytosis, erythema, purpura, vitiligos, bruises, moles, dark pores, sunburned regions, acne (pimples), pimple marks, pigmentation caused by abrasion or irritation, wrinkles, ephelides (freckles), tattoos, verrucae, scars and the like. A different factor type requires different remedy for discolored region 511.

The present exemplary embodiment facilitates restoration of discolored regions 511 by providing inclusive region 515 of makeup sheet 520, at a corresponding portion on its skin-side surface, with a medication (an active ingredient) corresponding to the factor type, in addition to a pigment material (a cosmetic material) which makes discolored regions 511 less noticeable.

Structure of Apparatus

Next, a description will be given of the structure of image processing apparatus 200.

Figure 7:
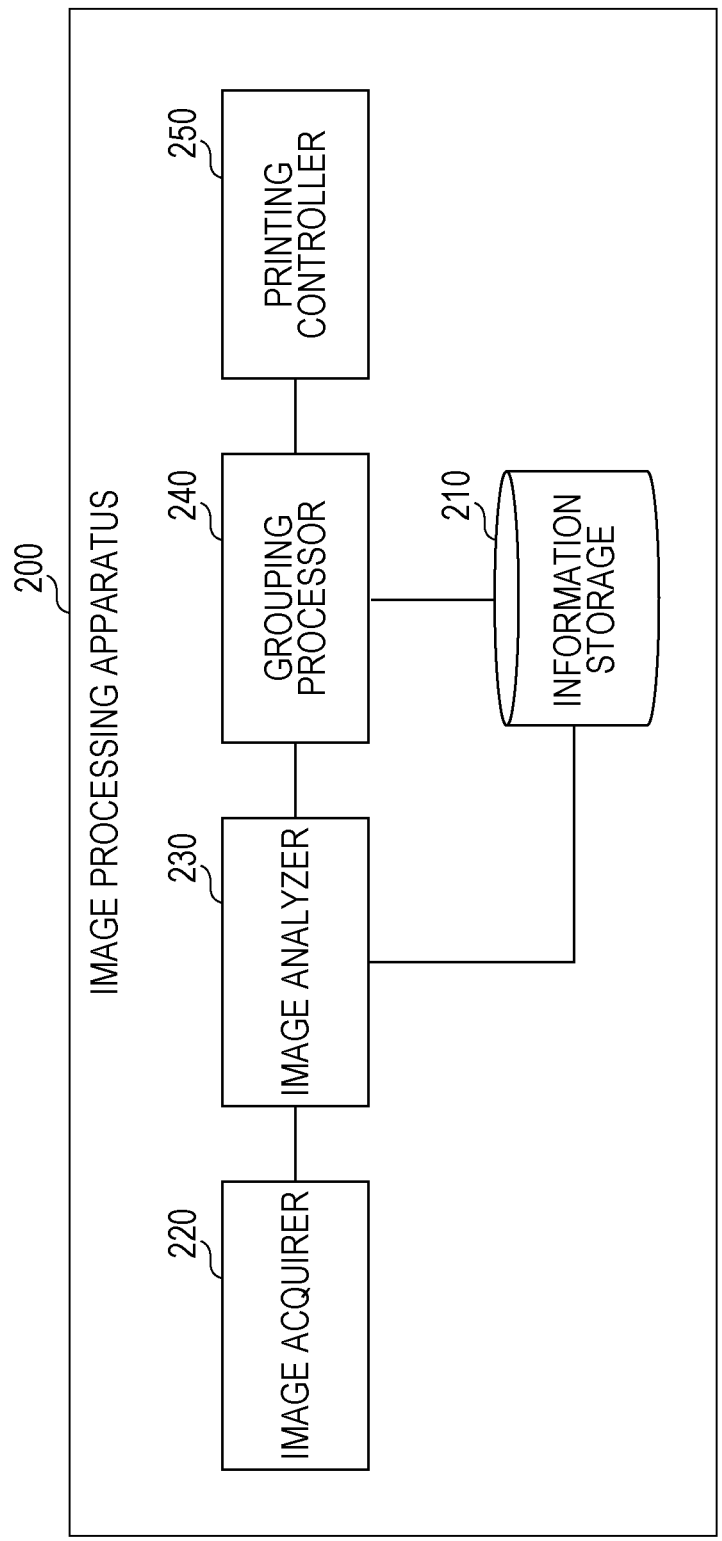
FIG. 7 is a block diagram showing an exemplary structure of an image processing apparatus according to the present disclosure.

FIG. 7 is a block diagram showing an exemplary structure of image processing apparatus 200.

In FIG. 7, image processing apparatus 200 includes information storage 210, image acquirer 220, image analyzer 230, grouping processor 240, and printing controller 250.

Information storage 210 previously stores various kinds of information necessary for image analyzer 230 to analyze an image, and various kinds of information necessary for grouping processor 240 to set inclusive region 515.

Image acquirer 220 includes, for example, the above-described camera 202 (see FIG. 1), and picks up an image with camera 202. Image acquirer 220 outputs the picked-up image to image analyzer 230. The picked-up image may include a facial image picked up from the face, and a skin image picked up from the skin.

Image analyzer 230 extracts facial parts from a facial image picked up from the face, and extracts an image of a skin region (a skin image) from the facial image, based on the positions of the extracted facial parts in the facial image. Further, image analyzer 230 extracts, from the skin image, discolored region 511 differing in color from the surrounding skin by at least a predetermined level, and the color of the skin surrounding discolored regions 511 (i.e., the surrounding color). Then, image analyzer 230 outputs, to grouping processor 240, analysis result information on the positions of the extracted facial parts, discolored regions 511, and the surrounding color, and the facial image.

Based on the analysis result information, grouping processor 240 groups a plurality of discolored regions 511, to set a region group. Grouping processor 240 further determines, for each set region group, inclusive region 515 that includes the region group. Then, grouping processor 240 outputs, to printing controller 250, grouping result information on the positions of the facial parts in the facial image and the position of inclusive region 515, and the facial image.

Note that, grouping processor 240 performs the grouping based on, for example, grouping rule information and group separating rule information stored in information storage 210. Further, grouping processor 240 performs the determination of inclusive region 515 based on, for example, inclusive region setting rule information stored in information storage 210. The grouping rule information, the group separating rule information, and the inclusive region setting rule information will be detailed later.

Printing controller 250 generates image data having a content of printing a pigment material that causes color of inclusive region 515 to approximate the surrounding color, on a region corresponding to inclusive region 515 in makeup sheet 520. Then, printing controller 250 transmits the generated image data to printer apparatus 300 via wireless communication and/or wired communication.

Note that, it is not essential for printing controller 250 to transmit the generated image data directly to printer apparatus 300, and may indirectly transmit the generated image data via other information recording device or the like. For example, printing controller 250 may record the generated image data on a recording medium such as a portable memory device, or may transmit the generated image data to a portable device (a smartphone, a tablet, a PC or the like). In this case, the user transmits the image data to printer apparatus 300 via the recording medium, the portable device or the like, and printing is appropriately performed as necessary based on a user's instruction or the like.

While not shown in the drawing, image processing apparatus 200 includes, for example, a CPU (a Central Processing Unit), a storage medium storing a control program such as ROM (Read Only Memory), working memory such as RAM (Random Access Memory), and a communication circuit. In this case, the functions of the units described above are realized by the CPU executing the control program.

Such image processing apparatus 200 can automatically extract discolored regions 511 on the face, and generate, using printer apparatus 300, makeup sheet 520 that has covering region 521 that collectively covers a plurality of discolored regions 511.

Contents of Various Kinds of Information

Here, a description will be given of the content of each of the grouping rule information, the group separating rule information, and the inclusive region setting rule information. The grouping rule information defines the determination criterion as to whether or not to group a plurality of discolored regions 511 into one region group. The group separating rule information defines the determination criterion as to whether or not to separate the once grouped discolored regions into a plurality of region groups. The inclusive region setting rule information defines the manner of setting inclusive region 515 to a region group.

FIG. 8 shows exemplary grouping rule information.

As shown in FIG. 8, grouping rule information 610 describes, for example, first and second grouping rules.

The first grouping rule is, for example, "group a plurality of discolored regions being spaced apart from each other by an interval being equal to or smaller than a predetermined threshold value". Here, the "interval" is a minimum distance between discolored regions 511 on the facial surface, calculated from, for example, a pixel distance on the facial image, or a distance from camera 202 to the face of user 400 (see FIG. 1) and the pixel distance. The distance from camera 202 to the face of user 400 can be estimated from, for example, the parallax of the facial parts obtained with a stereo camera, or the size of the face on the picked-up image.

The second grouping rule is, for example, "group a plurality of discolored regions differing in color from each other within a predetermined range". The difference in color is, for example, a distance on color coordinates in a predetermined color space such as RGB. That is, a plurality of discolored regions 511 differing in color from each other within a predetermined range are a plurality of discolored regions 511 in similar colors.

Note that, the content of grouping rule information 610 is not limited to such an example. For example, grouping rule information 610 may include the rule of grouping a plurality of discolored regions 511 differing from each other in proportion of RGB within a predetermined range, or the rule of grouping a plurality of discolored regions 511 of an identical factor type.

FIG. 9 shows exemplary group separating rule information.

As shown in FIG. 9, group separating rule information 620 describes, for example, first to third group separating rules.

The first group separating rule is, for example, "separate a region group based on color similarity when the difference in color exceeds a predetermined range". Here, "separate a region group based on color similarity" means that, for example, to separate a region group into region groups which are divided by a straight line in a predetermined color space, that is, to divide into groups each including the discolored regions of more similar colors.

The second group separating rule is, for example "separate a region group based on the factor type when a plurality of discolored regions differing from each other in factor type are included". Here, "separate a region group based on the factor type" is, for example, to separate a region group by the discolored regions differing from each other in proper treatment (active ingredient).

The third group separating rule is, for example, "separate a region group based on the position, color, or factor type when the number of the discolored regions in the region group is equal to or greater than a predetermined threshold value". Here, "separate a region group based on the position, color, or factor type" is, for example, to separate a region group where a plurality of discolored regions 511 are distributed by: dividing the region group with a line that passes through the center of the region group; separating the region group into region groups divided by a straight line in a predetermined color space; and separating the region group into region groups by the discolored regions differing from each other in proper treatment (active ingredient).

Note that, the content of group separating rule information 620 is not limited to such an example. For example, group separating rule information 620 may include the rule of separating a plurality of discolored regions 511 belonging to a region group and whose difference in proportion of RGB is outside a predetermined range to a different region group.

FIG. 10 shows exemplary inclusive region setting rule information.

As shown in FIG. 10, inclusive region setting rule information 630 describes, for example, first to third inclusive region setting rules.

The first inclusive region setting rule is, for example, "set a circular region (an elliptical region) that is circumscribes a region greater than the whole discolored regions as an inclusive region". Here, the "region greater than the whole discolored regions" is, for example, a region of a predetermined shape such as a circle, a quadrangle, or a pentagon by which discolored regions 511 are circumscribed, or a region obtained by expanding the region of such a shape outward by a predetermined width.

The second inclusive region setting rule is, for example, "set an elliptical region that includes the whole discolored regions by a minimum area as an inclusive region". Here, "an elliptical region that includes the whole discolored regions by a minimum area" is, for example, among possible ellipses which circumscribe a discolored region distributed region, which is formed by discolored regions 511 and regions between the discolored regions 511, an ellipse in which the area of regions except for discolored regions 511 is minimum.

The third inclusive region setting rule is, for example, "set an elliptical region that includes the discolored regions by a predetermined area ratio as an inclusive region". Here, the "elliptical region that includes the discolored regions by a predetermined area ratio" is, for example, a region of an ellipse obtained by shrinking or expanding an ellipse which circumscribes a discolored region distributed region formed by discolored regions 511 and regions between discolored regions 511, so that the ratio of the area of the occupying discolored regions 511 attains a predetermined area ratio.

Note that, the content of inclusive region setting rule information 630 is not limited to such an example. For example, group separating rule information 620 may include the rule of expanding the above-described discolored region distributed region outward by a predetermined width, smoothing the outer shape of the expanded region, and setting the smoothed region as inclusive region 515.

Operation of Apparatus Next, a description will be given of the operation of image processing apparatus 200.

Figure 11:
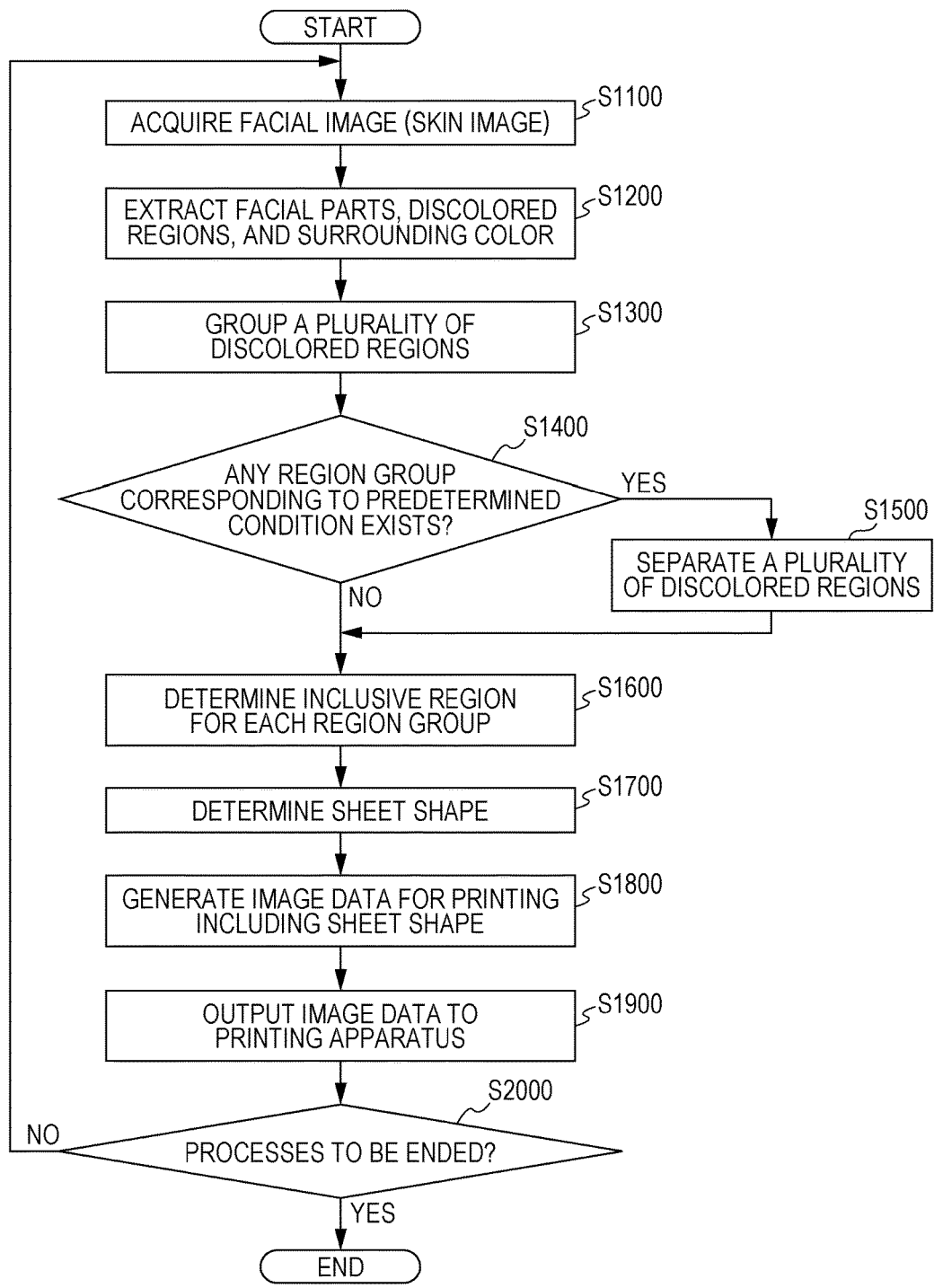
FIG. 11 is a flowchart showing an exemplary operation of the image processing apparatus according to the present disclosure.

FIG. 11 is a flowchart showing an exemplary operation of image processing apparatus 200.

In step S1100, image acquirer 220 acquires a facial image (a skin image).

In step S1200, image analyzer 230 extracts, from the facial image, the facial parts, discolored regions 511, and the surrounding color of each discolored region 511.

Specifically, for example, image analyzer 230 firstly acquires an image obtained by picking up an image of a predetermined color chart, and determines a correction value for color correction corresponding to the image pickup environment, based on the colors of the color chart in the image. Then, after performing color correction based on the determined correction value, image analyzer 230 detects the positions of the facial parts in the facial image by any known image recognition processing such as pattern matching. The scheme of extracting facial parts from an image is described in, for example, PTL 6, and therefore a detailed description thereof is not given herein.

Further, image analyzer 230 acquires, from the facial image excluding the facial parts, a region in a predetermined color range as a skin region. Image analyzer 230 then divides the skin region into discolored regions 511 and non-discolored region with reference to a predetermined pixel value (e.g., lightness), to extract discolored regions 511. Note that, here, image analyzer 230 may treat any discolored region 511 having an area equal to or smaller than a predetermined value as the non-discolored region. Then, image analyzer 230 extracts the average value of the non-discolored region near discolored regions 511 as the surrounding color. Note that, image analyzer 230 may extract discolored regions 511 and the surrounding color by the scheme described in PTL 1.

Further, image analyzer 230 may determine the factor type based on the disposition, size, color and the like of discolored regions 511.

For example, chloasma is characterized in its appearing horizontally symmetrically with reference to the center of the face, for example on the cheeks, the forehead, under the nose, and the chin. Accordingly, image analyzer 230 determines whether or not discolored regions 511 appear horizontally symmetrically based on the relative positions of discolored regions 511 with reference to the positions of the facial parts (e.g., the eyes). When discolored regions 511 appear, image analyzer 230 determines discolored regions 511 as chloasma.

Further, for example, ephelides (freckles) are distributed across the position of the nose as a multitude of small spots each measuring about 1 mm to 2 mm. Accordingly, image analyzer 230 determines that a multitude of small spots distributed at the nose position are ephelides.

Still further, image analyzer 230 may acquire various kinds of information such as the user's age, the user's race, the geographic area, the season and the like, and determine the factor type of discolored regions 511 based on the acquired information.

Note that, actual discolored regions 511 vary in shape and size. Accordingly, image analyzer 230 may convert each discolored region 511 to a simpler graphical region.

Figure 12:
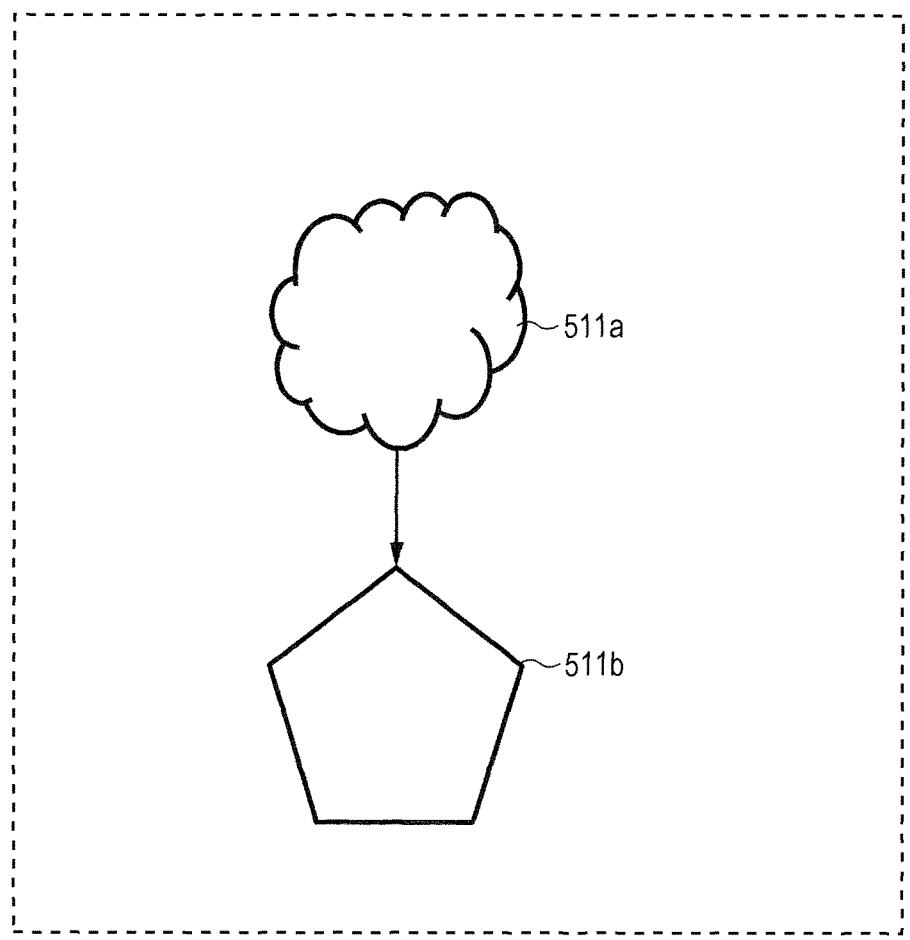
FIG. 12 illustrates an exemplary manner of converting the discolored region according to the present disclosure.

FIG. 12 shows an exemplary manner of converting discolored region 511.

As shown in FIG. 12, image analyzer 230 extracts discolored region 511a of indefinite shape and size from the skin image. Then, image analyzer 230 converts the extracted discolored region 511a to, for example, polygonal region 511b whose area and gravity are substantially as great as those of discolored region 511a. Image analyzer 230 then determines that the obtained polygonal region 511b is used as discolored region 511 in the following processes. The position of discolored region 511 is defined by, for example, coordinates of four or five vertices.

In step S1300, grouping processor 240 groups a plurality of discolored regions 511 based on grouping rule information 610 (see FIG. 8), to set a region group. Grouping processor 240 groups discolored regions 511, for example, putting higher priority on the distance based on the first grouping rule.

Note that, grouping processor 240 may perform the grouping based on just part of or all the rules described in grouping rule information 610. Further, grouping processor 240 may accept a setting instruction from the user about on what rule the grouping should be based.

Figure 13:
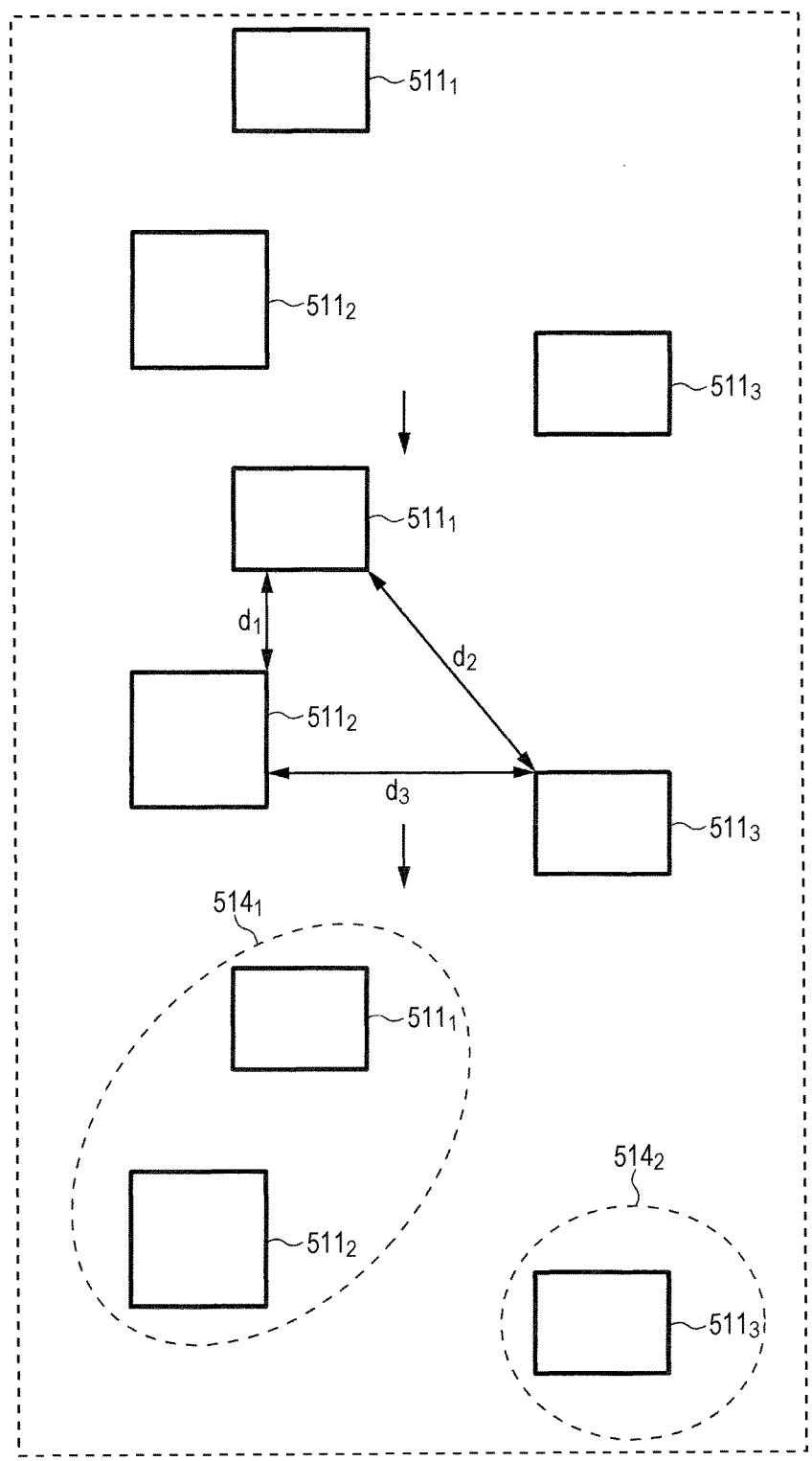
FIG. 13 illustrates an exemplary manner of grouping according to the present disclosure.

FIG. 13 shows an exemplary manner of grouping.

As shown in FIG. 13, for example, it is assumed that first to third discolored regions $511_1$ to $511_3$ exist. Distance $d_1$ between first discolored region $511_1$ and second discolored region $511_2$ is smaller than a predetermined threshold value, and distances $d_2$, $d_3$ respectively between first and second discolored regions $511_1$, $511_2$ and third discolored region $511_3$ are greater than a predetermined threshold value. In this case, grouping processor 240 sets first and second discolored regions $511_1$, $511_2$ to be first region group $514_1$, and sets third discolored region $511_3$ to be second region group $514_2$.

In step S1400 in FIG. 11, grouping processor 240 determines whether there exists any region group that corresponds to a predetermined condition defined by group separating rule information 620 (see FIG. 9). When there exists a region group that corresponds to a predetermined condition (S1400: YES), grouping processor 240 proceeds to step S1500. When there does not exist a region group that corresponds to a predetermined condition (S1400: NO), grouping processor 240 proceeds to step S1600, which will be described later.

In step S1500, grouping processor 240 separates, according to group separating rule information 620, a plurality of discolored regions 511 belonging to the region group into a plurality of region groups.

For example, when the number of discolored regions 511 belonging to one region group is equal to or greater than a predetermined threshold value, in step S1500, grouping processor 240 divides such a region group into a plurality of region groups. Further, when discolored regions 511 of different factor types belong to one region group, grouping processor 240 divides the region group for each factor type.

In step S1600, printing controller 250 determines, according to inclusive region setting rule information 630 (see FIG. 10), inclusive region 515 for each region group.

Figure 14:
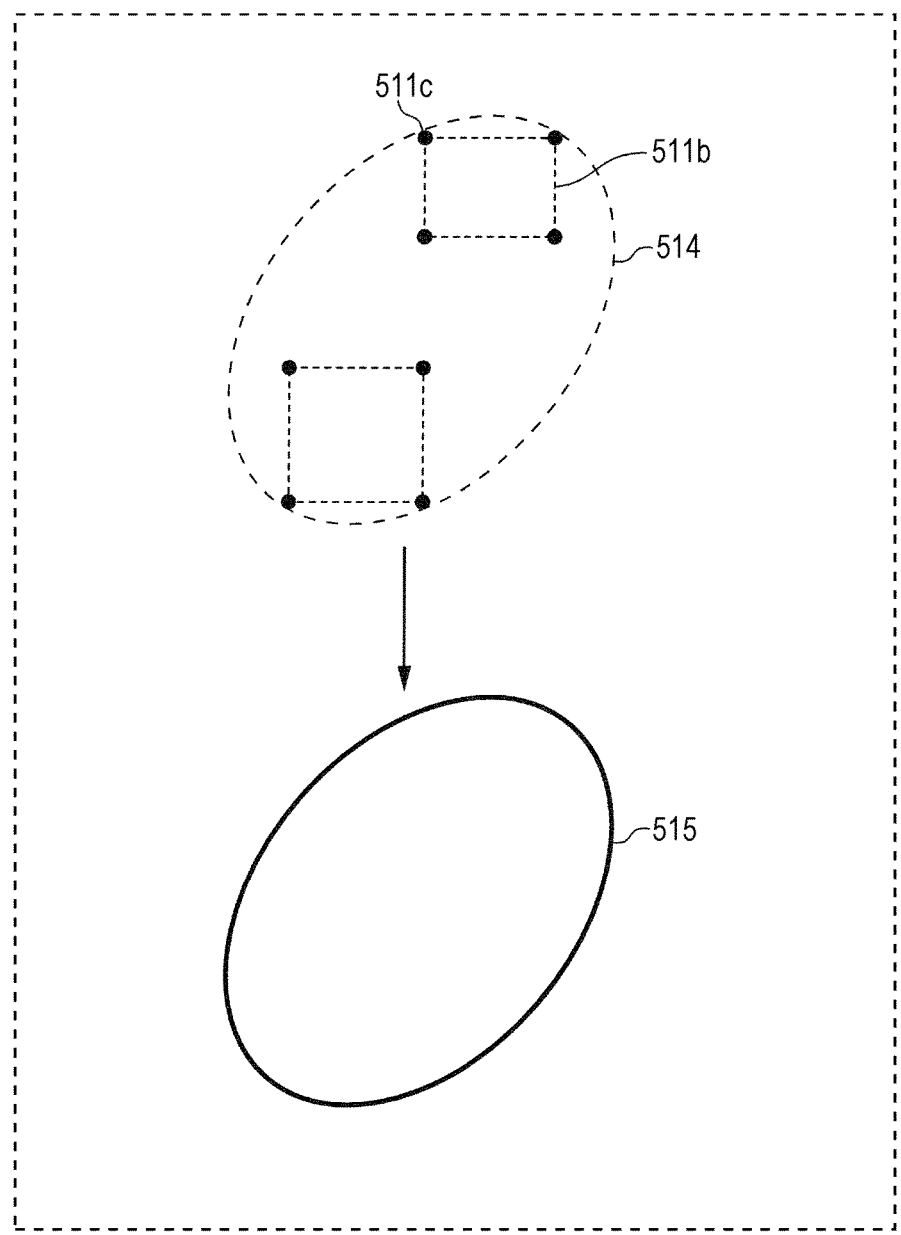
FIG. 14 illustrates an exemplary manner of setting an inclusive region according to the present disclosure.

FIG. 14 shows an exemplary manner of setting inclusive region 515.

As shown in FIG. 14, printing controller 250 firstly acquires vertices 511c of polygonal regions 511b of one or a plurality of discolored regions 511 belonging to an identical region group 514. Then, printing controller 250 calculates, for a group of points being all the vertices 511c belonging to an identical region group 514, an ellipse that contains the group of the points with a minimum square error as the outer shape of inclusive region 515.

Note that, after determining inclusive region 515 based on the predetermined rule, printing controller 250 may divide the original region group based on the determined inclusive region 515, to again determine inclusive region 515. For example, printing controller 250 again determines inclusive region 515 based on the rule "when the ratio in area of the non-discolored region to the discolored region in the inclusive region is equal to or greater than a predetermined threshold value, the original region group is divided to again set the inclusive region".

Further, printing controller 250 may superimpose the calculated ellipse on the facial image and display the result on display 203, and accept the user's instruction of correcting the shape, size, orientation and the like of the ellipse.

These processes can minimize the area of inclusive region 515 while absorbing attaching errors of makeup sheet 520. That is, these processes can reduce a wasteful consumption of a pigment material (a cosmetic material or the like) used in printing of covering region 521. Further, when an active ingredient such as a medication is contained, the active ingredient can be applied to a required range on the skin to enhance effect thereof.

In step S1700 of FIG. 11, printing controller 250 determines the sheet shape from the disposition of the facial parts. Specifically, printing controller 250 determines, as the sheet shape, a closed shape capable of covering the extracted one or a plurality of discolored regions 511 (or regions greater than discolored regions 511 by a predetermined width)

avoiding the positions of the facial parts (the nostrils, the eyes, the mouth, the eyebrows and the like) (for example, the shape such as makeup sheet 520 shown in FIGS. 2 to 6). Note that, since the face is three-dimensional and the sheet is basically two-dimensional, desirably the size of the sheet shape is limited to be equal to or smaller than 5 cm×5 cm, for example.

Further, printing controller 250 may cause the makeup sheet 520 to fit the three-dimensional shape of the face without the limitation in size of the sheet shape, by using makeup sheet 520 previously provided with cuts or by determining a sheet shape including cuts. For example, a plurality of cuts that run in the direction from the center of the face to the contour may be provided at the edge of the sheet. Further, as to the portion that covers the projecting part of the face such as the nose, cuts may be provided at the opposite sides of the projecting part. Alternatively, dotted-line-like cuts (slits) may be provided at a plurality of portions so that the sheet fits the three-dimensional shape of the face.

Note that, when there exist a plurality of region groups, printing controller 250 may display such region groups on display 203, and accept the user's instruction of specifying the region groups printed on one makeup sheet 520. A greater number of region groups being included in one makeup sheet 520 is advantageous in that greater number of discolored regions 511 can be covered by a single-time sheet attaching work. Further, a plurality of region groups being separately allocated to a greater number of makeup sheets 520 is advantageous in reducing the consumption of makeup sheet 520 and improving controllability over the attaching positions.

In step S1800, printing controller 250 generates image data for printing, which image data has a content of including the sheet shape determined in step S1700 and specifying formation of an image in inclusive region 515 in the surrounding color extracted in step S1200. The image data is, for example, data of CMYK (Cyan, Magenta, Yellow, and Key plate) color model.

Note that, printing controller 250 desirably generates image data in which the image dot density in covering region 521 becomes lower toward the outer circumference of covering region 521, that is, image data specifying fading (gradation) at the outer circumference of covering region 521. Alternatively, printing controller 250 may specify such fading on the portion outer than the outer circumference of covering region 521. Thus, printing controller 250 can control printer apparatus 300 so that covering region 521, which excellently blends with the non-discolored region in terms of color and shows natural finish, is printed on makeup sheet 520.

Further, printing controller 250 generates image data having a content of printing a medication containing an anti-inflammatory component, a lightening component or the like on the region on the skin-side surface of makeup sheet 520 corresponding to inclusive region 515. That is, printing controller 250 includes, in the image data, information specifying what medication is to be printed on each position in makeup sheet 520. In generating such image data, printing controller 250 refers to, for example, information describing the correspondence between the factor type and a proper medication previously stored in information storage 210.

For example, printing controller 250 determines to print, on inclusive region 515 corresponding to discolored regions 511 determined as chloasma, a hydroquinone-based medication in addition to a pigment material for masking the spots. Further, printing controller 250 determines to print, on inclusive region 515 corresponding to discolored regions 511 determined as ephelides, medication such as a UV absorber or a UV reflector in addition to a pigment material for masking the spots.

In such cases where a medication is also printed, the medication can be precisely applied to the skin by making processor 240 perform grouping based on the factor type. This not only reduces a wasteful consumption of a medication, but also improves the effect of applying the medication.

In step S1900, printing controller 250 outputs the generated image data to printer apparatus 300.

Then, in step S2000, image acquirer 220 determines whether or not it is instructed to end the processes by the user's operation or the like. When it is not instructed to end the processes (S2000: NO), image acquirer 220 returns the process to step S1100. When it is instructed to end the processes (S2000: YES), image acquirer 220 ends the series of processes.

With such operations, image processing apparatus 200 can automatically extract discolored regions 511 of the face, and generate, using printer apparatus 300, makeup sheet 520 including covering region 521 that collectively covers a plurality of discolored regions 511.

Note that, image processing apparatus 200 may accept an instruction by the user as to whether a plurality of makeup sheets 520 are to be printed in order one by one or at once.

Specific Example of Grouping and Inclusive Region

Next, some specific examples of grouping a plurality of discolored regions 511 and inclusive region 515 are shown.

FIGS. 15 to 18 show an exemplary manner of setting inclusive region 515.

Figure 15:
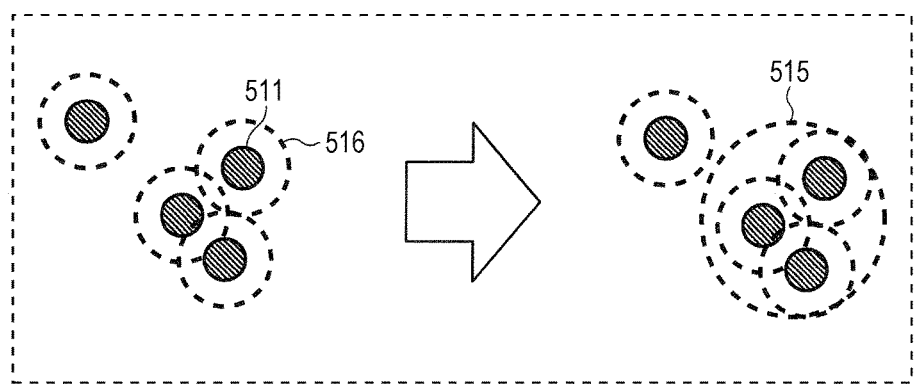
FIG. 15 illustrates a first exemplary manner of setting the inclusive region according to the present disclosure.

For example, it is assumed that the first grouping rule (see FIG. 8) and the first inclusive region setting rule (see FIG. 10) are applied. In this case, as shown in FIG. 15, among regions 516 respectively greater than discolored regions 511 (hereinafter referred to as "the extended discolored regions"), a plurality of extended discolored regions 516 being close to each other are grouped. Then, a circular region that circumscribes the grouped extended discolored regions 516 is determined as inclusive region 515.

Figure 16:
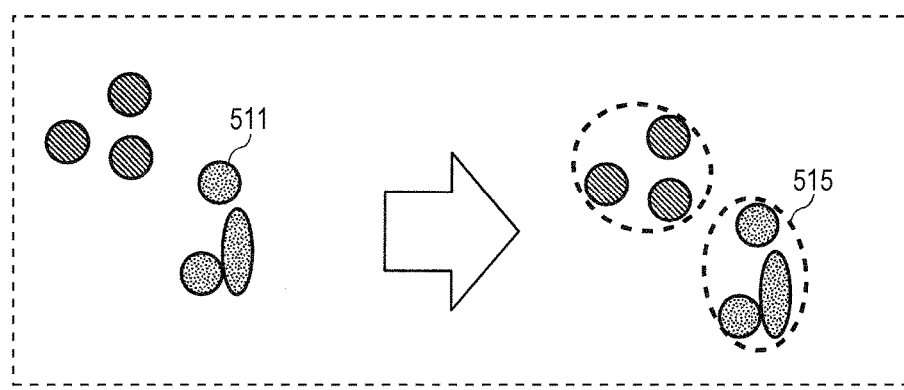
FIG. 16 illustrates a second exemplary manner of setting the inclusive region according to the present disclosure.

Further, for example, it is assumed that the second grouping rule (see FIG. 8) and the second inclusive region setting rule (see FIG. 10) are applied. In this case, as shown in FIG. 16, an elliptical region that includes a plurality of discolored regions 511 by a minimum area is determined as inclusive region 515.

Figure 17:
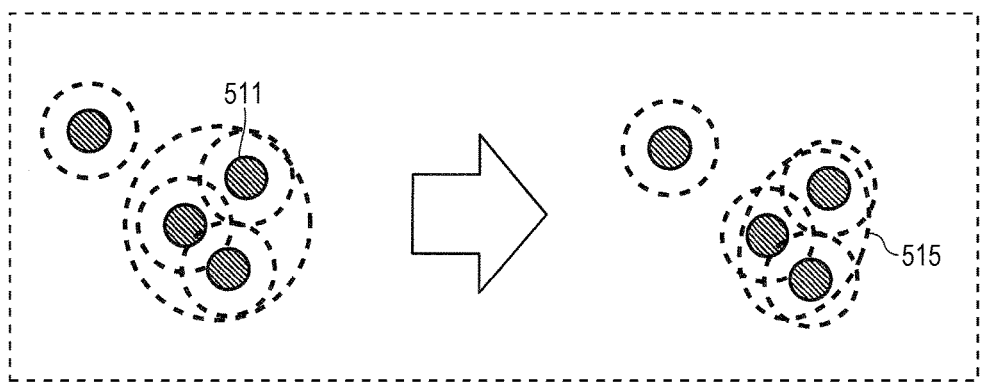
FIG. 17 illustrates a third exemplary manner of setting the inclusive region according to the present disclosure.

Still further, for example, it is assumed that the first grouping rule (see FIG. 8) and the third inclusive region setting rule (see FIG. 10) are applied. In this case, as shown in FIG. 17, an elliptical region that includes a plurality of discolored regions 511 and in which the ratio of the area of the occupying discolored regions 511 attains a predetermined value is determined as inclusive region 515.

Figure 18:
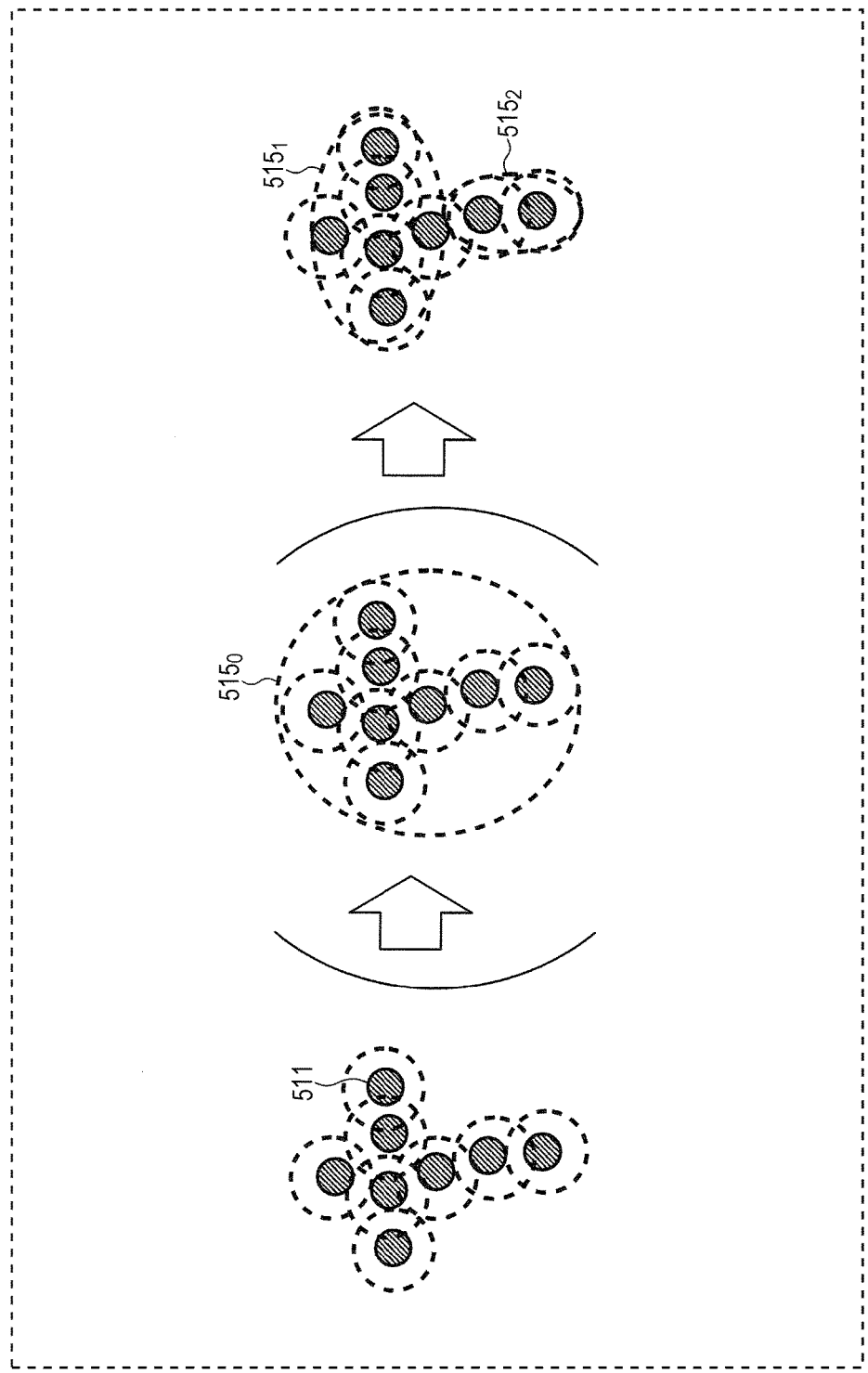
FIG. 18 illustrates a fourth exemplary manner of setting the inclusive region according to the present disclosure.

Still further, for example, it is assumed that firstly the first grouping rule (see FIG. 8), the third group separating rule (see FIG. 9), and the third inclusive region setting rule (see FIG. 10) are applied. In this case, as shown in FIG. 18, a multitude of discolored regions 511 in close proximity to each other are divided into two region groups in accordance with their positions. Then, two elliptical regions including their respective region groups and in each of which the ratio of the area of the occupying discolored regions 511 attains a predetermined value are determined as inclusive regions 515$_1$, 515$_2$.

Note that, as shown in FIG. 18, image processing apparatus 200 may once apply the first inclusive region setting rule (see FIG. 10) and generate an elliptical region that circumscribes extended discolored regions 516 of all the plurality of discolored regions 511 as inclusive region $515_O$. Then, image processing apparatus 200 may divide the region group on condition that the area of the occupying discolored regions 511 is smaller than a predetermined value.

Figure 19:
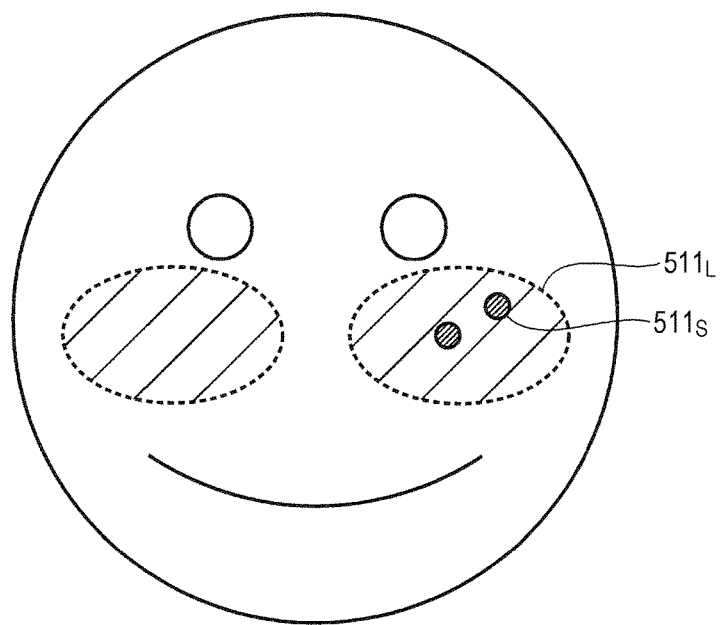
FIG. 19 illustrates other exemplary appearance of the skin according to the present disclosure.

FIG. 19 shows an exemplary appearance of skin in which intensively discolored regions 511 exist in lightly discolored region 511.

As shown in FIG. 19, it is assumed that small intensively discolored regions $511_S$ exist in large lightly discolored region $511_L$. Lightly discolored region $511_L$ is, for example, chloasma, and intensively discolored regions $511_S$ are, for example, senile lentigines. In other words, lightly discolored region $511_L$ is the region which differs in color from its surrounding by at least a first level, and intensively discolored regions $511_S$ are each the region which differs in color, in lightly discolored region $511_L$, from the surrounding of lightly discolored region $511_L$ by at least a second level which is greater than the first level.

In such a case, image analyzer 230 extracts lightly discolored region $511_L$ and intensively discolored regions $511_S$ as layers. That is, image analyzer 230 extracts a region including intensively discolored regions $511_S$ positioned inside as lightly discolored region $511_L$. That is, lightly discolored region $511_L$ includes regions which overlap intensively discolored regions $511_S$. Note that, the extraction of discolored regions 511 as layers may be performed based on the color of discolored regions 511, or based on the factor type of discolored regions 511.

Figure 20:
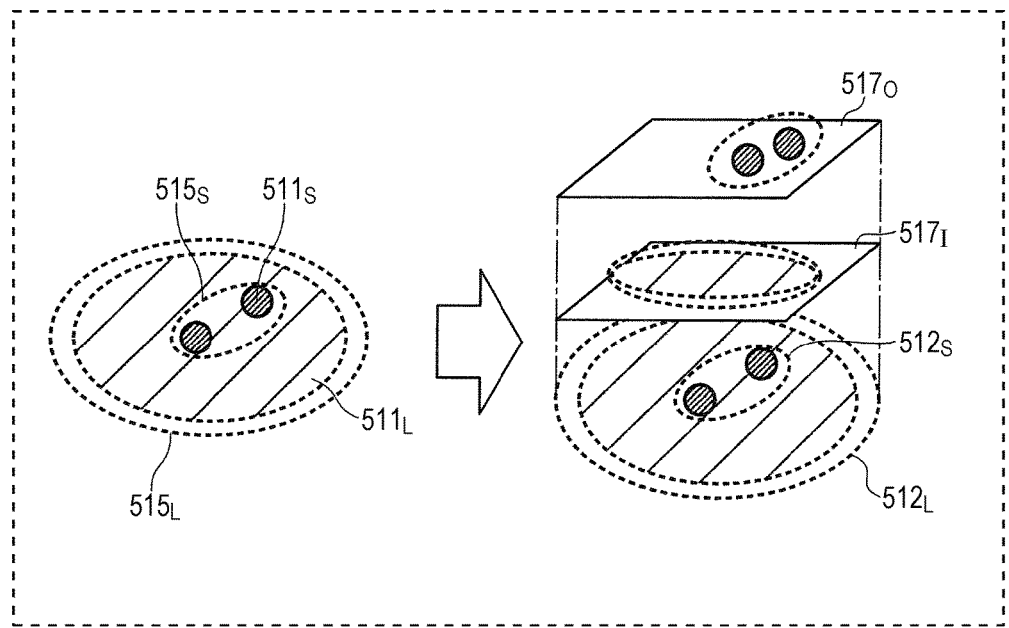
FIG. 20 illustrates an exemplary manner of setting the inclusive region and generating image data according to the present disclosure.

FIG. 20 shows an exemplary manner of setting inclusive regions 515 and generating the image data for the skin shown in FIG. 19.

As shown in FIG. 20, for example, for lightly discolored region $511_L$ and intensively discolored regions $511_S$, large inclusive region $515_L$ and small inclusive region $515_S$ are determined. Printing controller 250 treats these large inclusive region $515_L$ and small inclusive region $515_S$ as layers, to generate two image data $517_I$, $517_O$.

Image data $517_I$ is data that instructs printing of covering region $521_L$ that corresponds to large inclusive region $515_L$, on one side of makeup sheet 520 closer to the skin (the lower side). Image data $517_O$ is data that instructs printing of covering region $521_S$ that corresponds to small inclusive region $515_S$, on other side of makeup sheet 520 farther from the skin (the upper side).

In printing on the external surface of makeup sheet 520, printer apparatus 300 firstly prints image data $517_I$, and subsequently prints image data $517_O$ so as to be overlaid on image data $517_I$. In printing on the skin-side surface of makeup sheet 520, printer apparatus 300 firstly prints image data $517_O$, and subsequently prints image data $517_I$ so as to be overlaid on image data $517_O$.

In this manner, treating discolored regions as layers and determining inclusive region 515 and generating image data 517 enable efficient generation of makeup sheet 520. Further, in the above-described example, while intensively discolored regions $511_S$ are senile lentigines, they are also part of chloasma. Accordingly, when printer apparatus 300 prints not only a pigment material but also a medication, printer apparatus 300 can properly apply the medication.

Effect of Present Exemplary Embodiment

As has been described above, image processing apparatus 200 according to the present exemplary embodiment generates image data used in printing an image on makeup sheet 520. Image processing apparatus 200 includes image acquirer 220 that acquires a skin image, and image analyzer 230 that extracts discolored regions 511 and color of a region surrounding discolored regions 511 from the skin image. Image processing apparatus 200 further includes grouping processor 240 that groups a plurality of discolored regions 511, and determines inclusive region 515 for each region group which is a cluster of the grouped plurality of discolored regions 511, or one discolored region 511 not having been grouped. Then, image processing apparatus 200 further includes printing controller 250 that generates image data having a content of printing a pigment material that causes color of inclusive region 515 to approximate the surrounding color, on a region corresponding to inclusive region 515 in makeup sheet 520.

Thus, image processing apparatus 200 according to the present exemplary embodiment can implement makeup sheet 520 capable of more properly covering each discolored region 511 with a pigment material, coping with deviation in angle or position of a certain degree upon attachment on the skin. That is, image processing apparatus 200 can allow for greater tolerance in adjusting the angle or matching the coordinates upon attachment of makeup sheet 520. Therefore, image processing apparatus 200 can easily make a plurality of discolored regions 511 on the skin less noticeable.

Note that, it may be contemplated to generate image data for printing a pigment material on makeup sheet 520 over a largest possible area independently of the disposition of discolored regions 511. However, in this case, the face may appear as if foundation is evenly thickly applied thereto. Accordingly, image processing apparatus 200 according to the present exemplary embodiment can make discolored regions 511 less noticeable while keeping the natural appearance of the skin.

Variation of Present Exemplary Embodiment

Note that, the scheme of extracting discolored regions 511, the scheme of determining the factor type, the scheme of grouping discolored regions 511, the scheme of determining inclusive region 515, the scheme of determining a printing material, and the printing scheme are not limited to those described in the foregoing. For example, as the scheme of extracting discolored regions 511, the scheme of determining the factor type, and the scheme of grouping discolored region 511, known classification scheme, pattern recognition scheme, clustering scheme, and optimization scheme can be employed.

The known classification scheme may be, for example, the decision tree analysis, the neural networks (including deep learning), and the naive Bayes. The known pattern recognition scheme may be, for example, the neural networks (including deep learning) and the support vector machine (SVM). The known clustering scheme may be, for example, the k-Nearest Neighbor (k-NN), the k-means, and the hierarchical clustering. The known optimization scheme may be, for example, the genetic algorithm.

Further, the scheme of determining the sheet shape is not limited to the foregoing example. For example, printing controller 250 may form a handle for the user to grasp makeup sheet 520, at part of makeup sheet 520 excluding covering region 521.

Still further, the scheme of generating image data is not limited to the foregoing example. For example, image processing apparatus 200 may acquire, with image analyzer 230, the face feature points such as the corners of the eyes and the corners of the mouth, and may determine, with printing controller 250, the shape of the makeup sheet that is extended to the positions in close proximity to these face feature points. Then, printing controller 250 may generate image data having a content of printing, on makeup sheet 520, markers for alignment with the face feature points. Note that, when makeup sheet 520 that is kept applied on the skin is employed, desirably, the markers are printed on the supporter or may be made of a material that becomes invisible with time by temperatures or drying.

Still further, printing controller 250 may generate image data that has a content of providing gradation in color or lightness to covering region 521. In this case, image analyzer 230 or printing controller 250 extracts surrounding color for each of a plurality of positions around inclusive region 515, and generates image data of covering region 521 in which color or lightness smoothly varies based on the extracted plurality of surrounding colors.

Still further, image processing apparatus 200 may output (display, audio output, transmit) various kinds of information other than image data. For example, image processing apparatus 200 may cooperate with an external display apparatus such as a user's smartphone, and may suggest effective internal medicine or meal to the user for restoration of discolored regions 511. For example, in case of chloasma, image processing apparatus 200 may suggest that the user take tranexamic acid or vitamin C.

Still further, an image processed by image processing apparatus 200 is not limited to a facial image, and may be, for example, an image picked up from the back of the hand or the skin of the arm.

Still further, part of the structure of image processing apparatus 200 may be physically separated from other part of image processing apparatus 200. In this case, each of these plurality of separated parts must be equipped with a communicator for establishing communication with each other. For example, part of the functions of image processing apparatus 200 may be implemented by cloud migration. Further, image processing apparatus 200 and printer apparatus 300 may be integrally structured. Still further, disposition of image processing apparatus 200 and printer apparatus 300 is not limited to the foregoing example. For example, printer apparatus 300 may be disposed remotely from image processing apparatus 200, such as at a printing factory, and may receive image data via a communication network such as the Internet.

Summary of Present Disclosure An image processing apparatus of the present disclosure is an image processing apparatus that generates an image data used in printing an image on a sheet being attachable to skin. The image processing apparatus includes: an image acquirer that acquires a skin image picked up from the skin; an image analyzer that extracts, from the skin image, a discolored region differing in color from surrounding skin by at least a predetermined level, and surrounding color being color of the skin surrounding the discolored region; a grouping processor that groups a plurality of the discolored regions, and determines an inclusive region for each region group which is a cluster of the grouped plurality of discolored regions or the one discolored region not having been grouped, to include the one or a plurality of the region groups; and a printing controller that generates the image data having a content of printing a pigment material that causes color of the inclusive region to approximate the surrounding color, on a region corresponding to the inclusive region in the sheet.

Note that, in the image processing apparatus, when the skin image is a facial image picked up from a face, the image analyzer may extract facial parts from the facial image, and the grouping processor may perform the grouping and the determination of the inclusive region based on positions of the facial parts and positions of the discolored regions.

Further, in the image processing apparatus, the printing controller may determine, based on the positions of the facial parts and a position of the inclusive region, a shape of the sheet on the face, and may output the image data that includes an instruction to form the sheet in the determined shape.

Still further, in the image processing apparatus, the grouping processor may determine the region group based on a distance between the plurality of discolored regions.

Still further, in the image processing apparatus, the grouping processor may determine the region group based on respective colors of the plurality of discolored regions.

Still further, in the image processing apparatus, the grouping processor may determine a shape of the inclusive region based on disposition of one or a plurality of the discolored regions belonging to the region group.

Still further, in the image processing apparatus, the grouping processor may determine, for each of the discolored regions, a factor type of the discolored region, and may determine the region group based on the determined factor type. The printing controller may generate the image data having a content of providing the inclusive region with a medication corresponding to the factor type.

Still further, in the image processing apparatus, when the skin includes a first discolored region differing in color from its surrounding by at least a first level and a second discolored region positioned in the first discolored region and differing in color from the surrounding of the first discolored region by at least a second level which is greater than the first level, the image analyzer may extract the first discolored region and the second discolored region from the skin image, the grouping processor may perform the grouping separately between the first discolored region and the second discolored region, and may determine a first type of the inclusive region corresponding to the first discolored region and a second type of the inclusive region corresponding to the second discolored region, the printing controller may generate, a first type of the image data having a content of printing a pigment material that causes color of the first type of the inclusive region to approximate the surrounding color, on a region corresponding to the first type of the inclusive region in the sheet, and a second type of the image data having a content of printing a pigment material that causes color of the second type of the inclusive region to approximate the surrounding color, on a region corresponding to the second type of the inclusive region in the sheet.

Still further, in the image processing apparatus, the printing controller may output the image data used by a printer that performs the printing on the sheet.

An image processing method of the present disclosure is an image processing method of generating image data used in printing an image on a sheet being attachable to skin. The image processing method includes: acquiring a skin image picked up from the skin; extracting, from the skin image, a discolored region differing in color from surrounding skin by at least a predetermined level, and surrounding color being color of the skin surrounding the discolored region; grouping a plurality of the discolored regions, and determining an inclusive region for each region group which is a cluster of the grouped plurality of discolored regions or one discolored region not having been grouped, to include the one or a plurality of the region groups; and generating the image data having a content of printing a pigment material that causes color of the inclusive region to approximate the surrounding color, on a region corresponding to the inclusive region in the sheet.

The image processing apparatus and the image processing method according to the present disclosure are useful as an image processing apparatus and an image processing method capable of easily making a plurality of discolored regions of the skin less noticeable.

What is claimed is:

1. An image processing apparatus that generates an image data used in printing an image on a sheet being attachable to skin, the image processing apparatus comprising:
    an image acquirer that acquires a skin image picked up from the skin;
    an image analyzer that extracts, from the skin image, a discolored region differing in color from surrounding skin by at least a predetermined level, and surrounding color being color of the skin surrounding the discolored region;
    a grouping processor that groups a plurality of the discolored regions, and determines an inclusive region for each region group which is a cluster of the grouped plurality of discolored regions or the one discolored region not having been grouped, to include the one or a plurality of the region groups; and
    a printing controller that generates the image data having a content of printing a pigment material that causes color of the inclusive region to approximate the surrounding color, on a region corresponding to the inclusive region in the sheet.

2. The image processing apparatus according to claim 1, wherein
    when the skin image is a facial image picked up from a face,
    the image analyzer extracts facial parts from the facial image, and
    the grouping processor performs the grouping and the determination of the inclusive region based on positions of the facial parts and positions of the discolored regions.

3. The image processing apparatus according to claim 2, wherein
    the printing controller determines, based on the positions of the facial parts and a position of the inclusive region, a shape of the sheet on the face, and outputs the image data that includes an instruction to form the sheet in the determined shape.

4. The image processing apparatus according to claim 1, wherein
    the grouping processor determines the region group based on a distance between the plurality of discolored regions.

5. The image processing apparatus according to claim 1, wherein
    the grouping processor determines the region group based on respective colors of the plurality of discolored regions.

6. The image processing apparatus according to claim 1, wherein
    the grouping processor determines a shape of the inclusive region based on disposition of one or a plurality of the discolored regions belonging to the region group.

7. The image processing apparatus according to claim 1, wherein
    the grouping processor determines, for each of the discolored regions, a factor type of the discolored region, and determines the region group based on the determined factor type, and
    the printing controller generates the image data having a content of providing the inclusive region with a medication corresponding to the factor type.

8. The image processing apparatus according to claim 1, wherein
    when the skin includes a first discolored region differing in color from its surrounding by at least a first level and a second discolored region positioned in the first discolored region and differing in color from the surrounding of the first discolored region by at least a second level which is greater than the first level, the image analyzer extracts the first discolored region and the second discolored region from the skin image,
    the grouping processor performs the grouping separately between the first discolored region and the second discolored region, and determines a first type of the inclusive region corresponding to the first discolored region and a second type of the inclusive region corresponding to the second discolored region,
    the printing controller generates, a first type of the image data having a content of printing a pigment material that causes color of the first type of the inclusive region to approximate the surrounding color, on a region corresponding to the first type of the inclusive region in the sheet, and a second type of the image data having a content of printing a pigment material that causes color of the second type of the inclusive region to approximate the surrounding color, on a region corresponding to the second type of the inclusive region in the sheet.

9. The image processing apparatus according to claim 1, wherein
    the printing controller outputs the image data used by a printer that performs the printing on the sheet.

10. An image processing method for generating image data used in printing an image on a sheet being attachable to skin, the image processing method comprising:
    acquiring a skin image picked up from the skin;
    extracting, from the skin image, a discolored region differing in color from surrounding skin by at least a predetermined level, and surrounding color being color of the skin surrounding the discolored region;
    grouping a plurality of the discolored regions, and determining an inclusive region for each region group which is a cluster of the grouped plurality of discolored regions or one discolored region not having been grouped, to include the one or a plurality of the region groups; and
    generating the image data having a content of printing a pigment material that causes color of the inclusive region to approximate the surrounding color, on a region corresponding to the inclusive region in the sheet.

* * * * *